United States Patent
Merkel et al.

(10) Patent No.: US 9,752,891 B2
(45) Date of Patent: Sep. 5, 2017

(54) WEARABLE FITNESS DEVICE AND FITNESS DEVICE INTERCHANGEABLE WITH PLURAL WEARABLE ARTICLES

(71) Applicants: Carolyn M. Merkel, North Haledon, NJ (US); Barbara J. Merkel, Culver City, CA (US)

(72) Inventors: Carolyn M. Merkel, North Haledon, NJ (US); Barbara J. Merkel, Culver City, CA (US)

(*) Notice: Subject to any disclaimer, the term of this patent is extended or adjusted under 35 U.S.C. 154(b) by 155 days.

(21) Appl. No.: 14/452,918

(22) Filed: Aug. 6, 2014

(65) Prior Publication Data
US 2014/0350702 A1 Nov. 27, 2014

Related U.S. Application Data

(63) Continuation of application No. 12/378,684, filed on Feb. 17, 2009, now abandoned, which is a
(Continued)

(51) Int. Cl.
| | |
|---|---|
| A61B 5/11 | (2006.01) |
| G01C 22/00 | (2006.01) |
| A43B 3/00 | (2006.01) |
| A61B 5/00 | (2006.01) |
| A61B 5/22 | (2006.01) |

(52) U.S. Cl.
CPC .............. *G01C 22/006* (2013.01); *A43B 3/00* (2013.01); *A43B 3/0005* (2013.01); *A61B 5/11* (2013.01); *A61B 5/6804* (2013.01); *A61B 5/6828* (2013.01); *A61B 5/6831* (2013.01); *A61B 5/222* (2013.01); *A61B 2562/0219* (2013.01); *A63B 2220/17* (2013.01); *A63B 2220/836* (2013.01)

(58) Field of Classification Search
CPC ........................... A61B 5/1118; G01C 22/006
USPC ............................................ 600/595; 63/1.13
See application file for complete search history.

(56) References Cited

U.S. PATENT DOCUMENTS

| | | | |
|---|---|---|---|
| 3,695,494 A | 10/1972 | Bruner | |
| 3,824,783 A | 7/1974 | Nadeau | |

(Continued)

FOREIGN PATENT DOCUMENTS

| | | | |
|---|---|---|---|
| JP | 2-300883 A | 12/1990 | |
| JP | 2-310689 A | 12/1990 | |

(Continued)

OTHER PUBLICATIONS

European Patent Application No. EP 06 80 0629, European Search Report, Jan. 14, 2011 (6 pages).

(Continued)

*Primary Examiner* — Michael C Stout
*Assistant Examiner* — Nicholas E Kolderman
(74) *Attorney, Agent, or Firm* — Abelman, Frayne & Schwab

(57) ABSTRACT

The present invention relates to a fitness device comprising a display having plurality of lights that are configured for illumination as fitness intervals are achieved by a user. The fitness device is interchangeable with plural wearable articles. This functional fitness device allows a user to track their steps while at work, shopping, an evening out, or anytime one is on the move, even when it is interchanged between different wearable articles.

13 Claims, 17 Drawing Sheets

Related U.S. Application Data continuation-in-part of application No. 11/497,572, filed on Aug. 1, 2006, now abandoned.

(60) Provisional application No. 60/704,365, filed on Aug. 1, 2005.

(56) References Cited

U.S. PATENT DOCUMENTS

| | | | |
|---|---|---|---|
| 3,889,323 A | | 6/1975 | Reith |
| 4,129,125 A | * | 12/1978 | Lester .................. A61B 5/0002 374/142 |
| 4,371,945 A | * | 2/1983 | Karr ..................... G01C 22/006 235/105 |
| 4,637,606 A | * | 1/1987 | Hunn ....................... A63B 5/20 482/82 |
| 4,651,446 A | | 3/1987 | Yukawa et al. |
| 5,931,764 A | | 8/1999 | Freeman et al. |
| 6,080,690 A | | 6/2000 | Lebby et al. |
| 6,241,684 B1 | | 6/2001 | Amano et al. |
| 6,298,314 B1 | | 10/2001 | Blackadar et al. |
| 6,397,151 B1 | | 5/2002 | Yamagishi et al. |
| 6,560,903 B1 | | 5/2003 | Darley |
| 6,836,524 B1 | | 12/2004 | Lee |
| 6,898,550 B1 | | 5/2005 | Blackadar et al. |
| 7,008,350 B1 | | 3/2006 | Yamazski et al. |
| 7,057,551 B1 | * | 6/2006 | Vogt ................... A63B 69/0028 342/357.57 |
| 7,398,151 B1 | * | 7/2008 | Burrell ............... A63B 24/0062 342/357.75 |
| 7,596,891 B2 | * | 10/2009 | Carnes et al. .................. 36/132 |
| 8,795,137 B2 | * | 8/2014 | Ellis et al. ....................... 482/8 |
| 2002/0019296 A1 | * | 2/2002 | Freeman ................ A63F 13/02 482/4 |
| 2002/0023289 A1 | * | 2/2002 | Arias ..................... A41D 23/00 2/279 |
| 2004/0007017 A1 | | 1/2004 | Flaherty |
| 2004/0102931 A1 | * | 5/2004 | Ellis ..................... A61B 5/1038 702/188 |
| 2004/0194502 A1 | * | 10/2004 | Ma ....................... A44C 5/2095 63/3.1 |
| 2005/0078274 A1 | * | 4/2005 | Howell .................. G02C 11/10 351/158 |
| 2007/0260421 A1 | * | 11/2007 | Berner ................. A43B 3/0005 702/160 |

FOREIGN PATENT DOCUMENTS

| | | | |
|---|---|---|---|
| JP | 4-324590 A | | 11/1992 |
| JP | 6-300582 A | | 10/1994 |
| JP | 9-185693 A | | 7/1997 |
| JP | 10-227629 | | 8/1998 |
| JP | 2001-108479 | | 4/2001 |
| JP | 2001-333804 | | 4/2001 |
| JP | 2002-058507 | | 2/2002 |
| JP | 2003-308511 A | | 10/2003 |
| JP | 2007334790 A | * | 12/2007 |
| WO | 99/18480 A1 | | 4/1999 |

OTHER PUBLICATIONS

Japanese Patent Application No. 2008-525126, Japanese Office Action, Jan. 14, 2011 (6 pages).

"See How Easy It Is to Consult Ankle Watch", The Pittsburg Press, Friday Evening Night Edition, Jan. 7, 1916, pp. 1 and 26.

Kremer, Esther Gross, "Fashion Compass We'll Point You in a New Direction", New York Daily News, Apr. 15, 2001, p. 12.

Kremer, Esther Gross, "Fashion Compass We'll Point You in a New Direction", New York Daily News, Apr. 15, 2001, p. 12 (text of article).

PCT ISA and Written Opinion, PCT/US2006/29980, Sep. 13, 2007, pp. 1-7.

"Pedometers Help Step Up Your Health", Mayo Clinic Women's HealthSource, Jun. 11, 2004, available from: http://www.mayoclinic.org/news2004-mchi/2310.html, as printed on Jul. 3, 2006 (p. 1).

"America on the Move", Active Living, available from: http://aon.americaonthemove.org/site/c.hiJRKOPFJpH/b.1311167/k.8725/active_living.htm, as printed on Jul. 30, 2006 (p. 1).

Wilson D.B. et al., "Using exercise for risk reduction in African American breast cancer survivors: a community-based pilot study" [Abstract], Prev Chronic Dis [serial online], Apr. 2004 [date cited]; available from: http://www.cdc.gov/pcd/issues/2004/apr/03_0034r.htm, as printed on Jul. 30, 2005 (pp. 1-2).

"General Guidance for Pedometer Use", Division of Nutrition Research Coordination (DNRC), Nov. 19, 2004; available from: http://dnrc.nih.gov/move/pedometer_use,htm, as printed on Jul. 30, 2006 (pp. 1-2).

Marshall et al., "Watch Your Step: Pedometers and Physical Activity", WellSpring, Winter 2003, vol. 14, No. 2, available from: http://www.centre4activeliving/ca/publications/wellspring/2003/Spring/How TheyWork.html, as printed on Jul. 30, 2006 (p. 1).

Arrigio, "Picking a pedometer—Finding one you can count on can involve many steps on the road to fitness", Knight Ridder, Jun. 1, 2003, available from: http://www.jsonline.com/story/index_aspx?id=144671, as printed on Jul. 30, 2006, pp. 1-3).

Mesmic Inc. Model MXC6202G/H/M/N (North Andover, MA), specification sheet Rev. B dated Nov. 10, 2005, pp. 1-10.

* cited by examiner

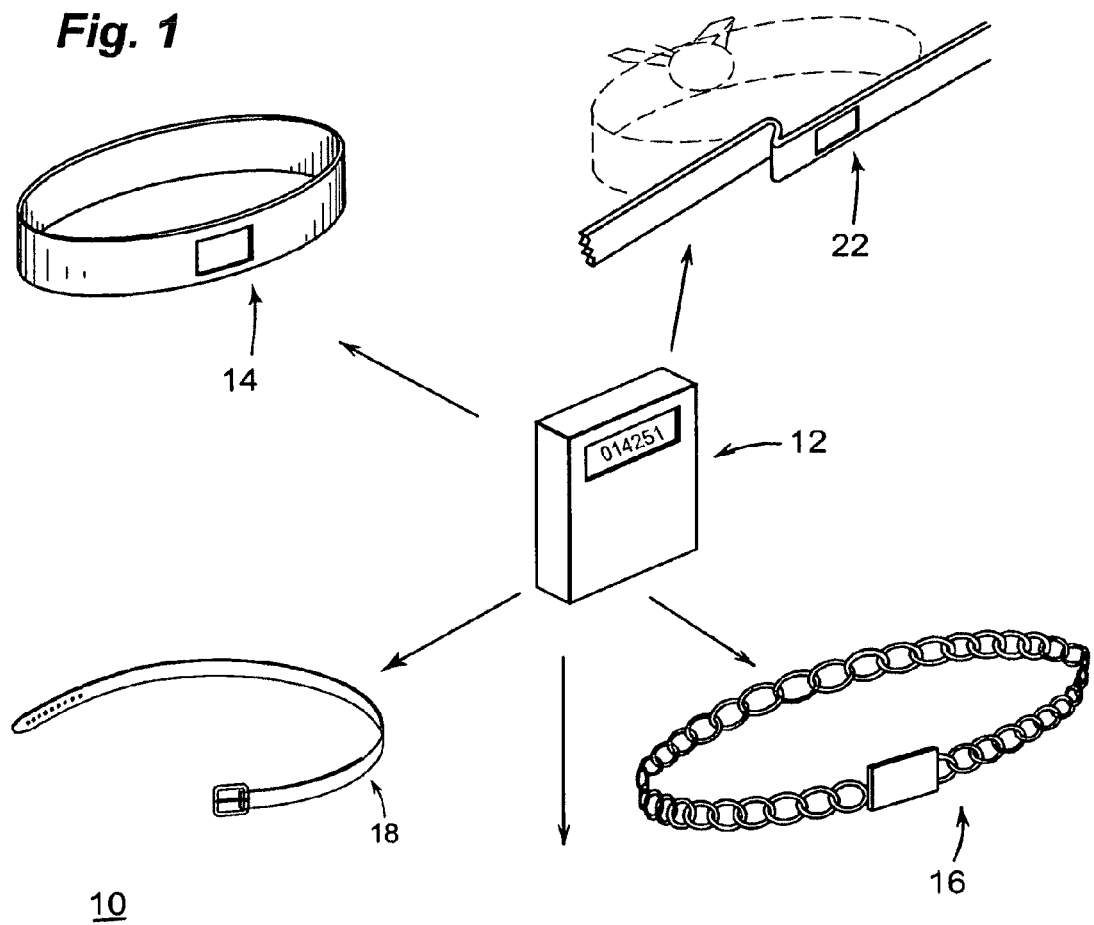
Fig. 1
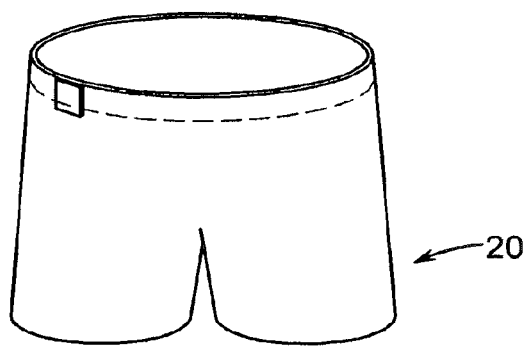

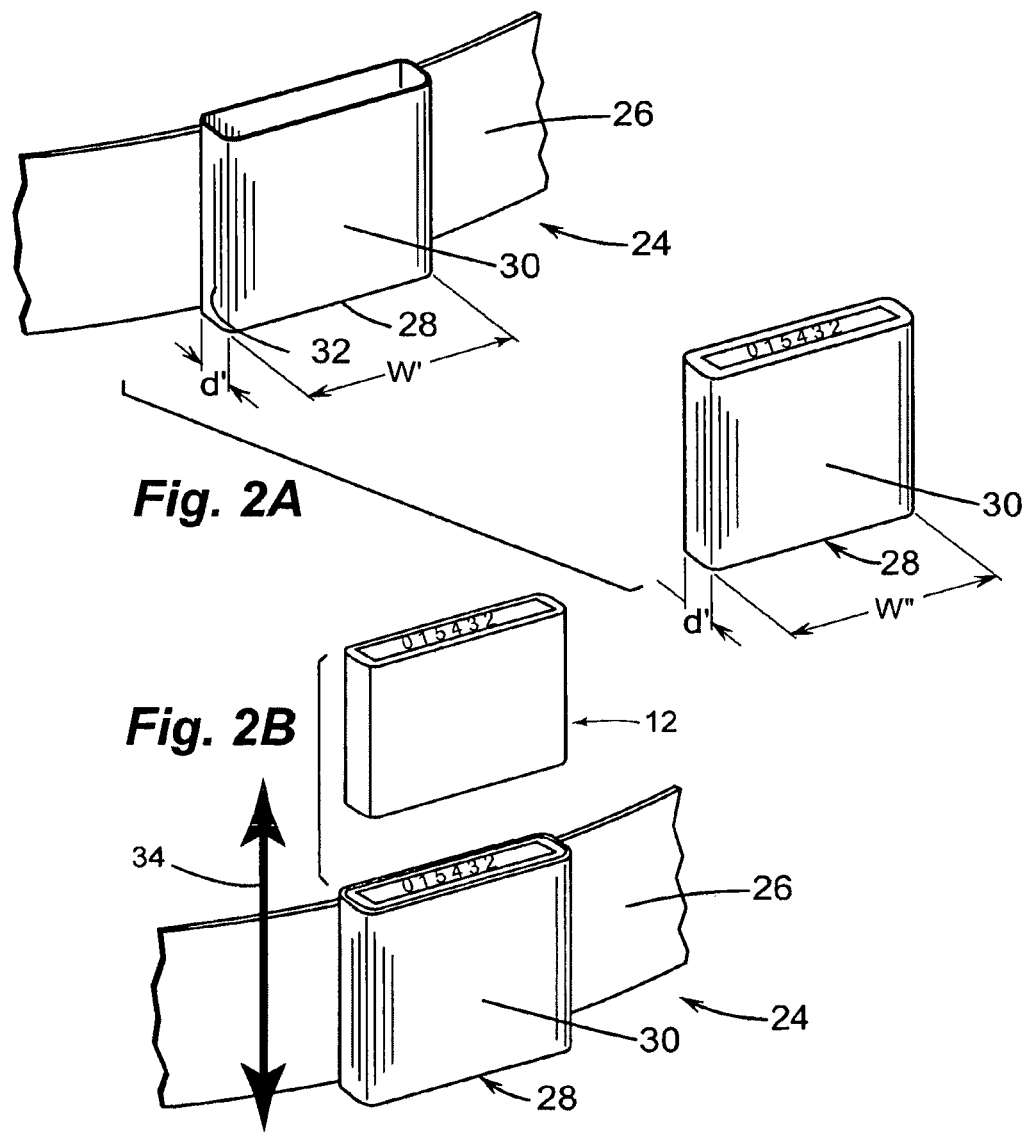

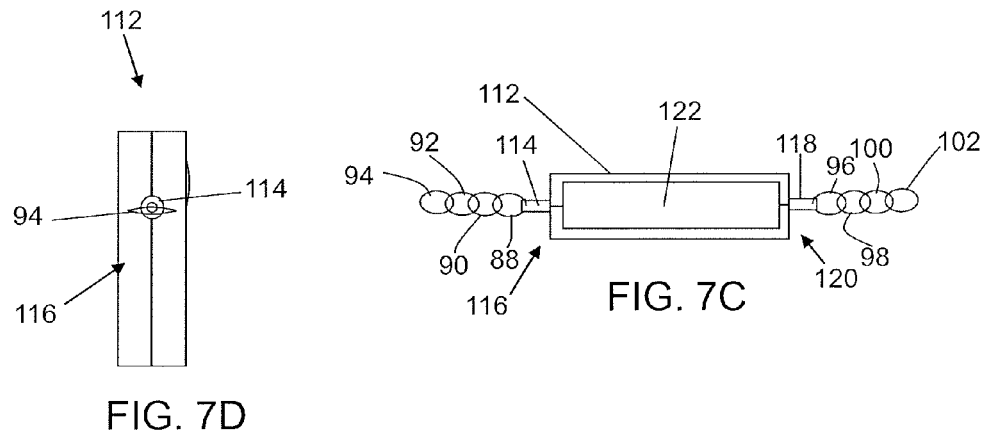
FIG. 7D
FIG. 7C
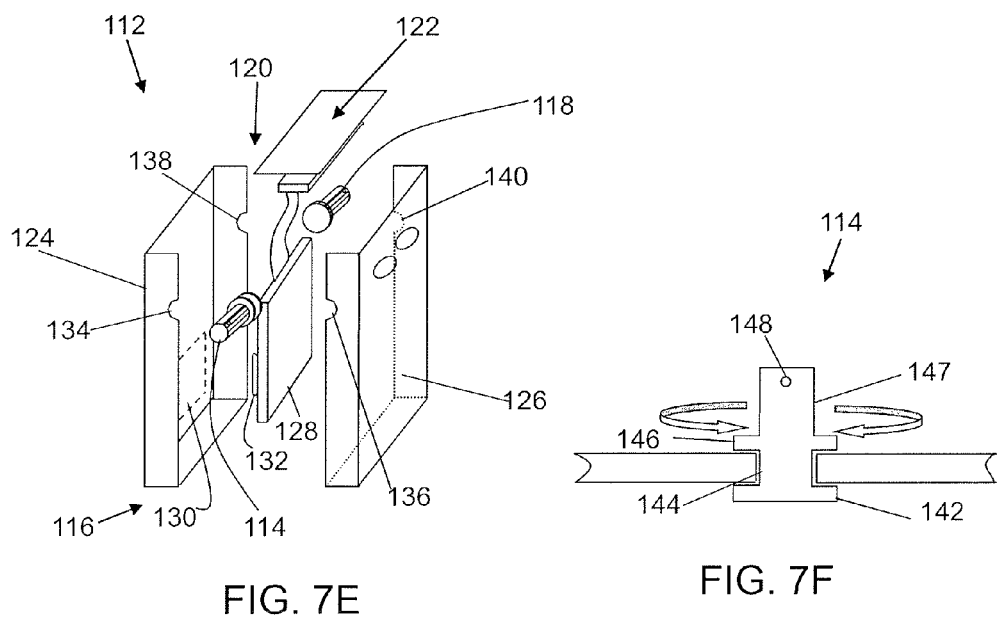
FIG. 7E
FIG. 7F

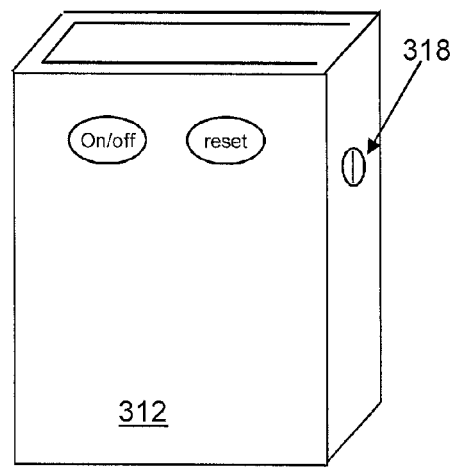
FIG. 9A
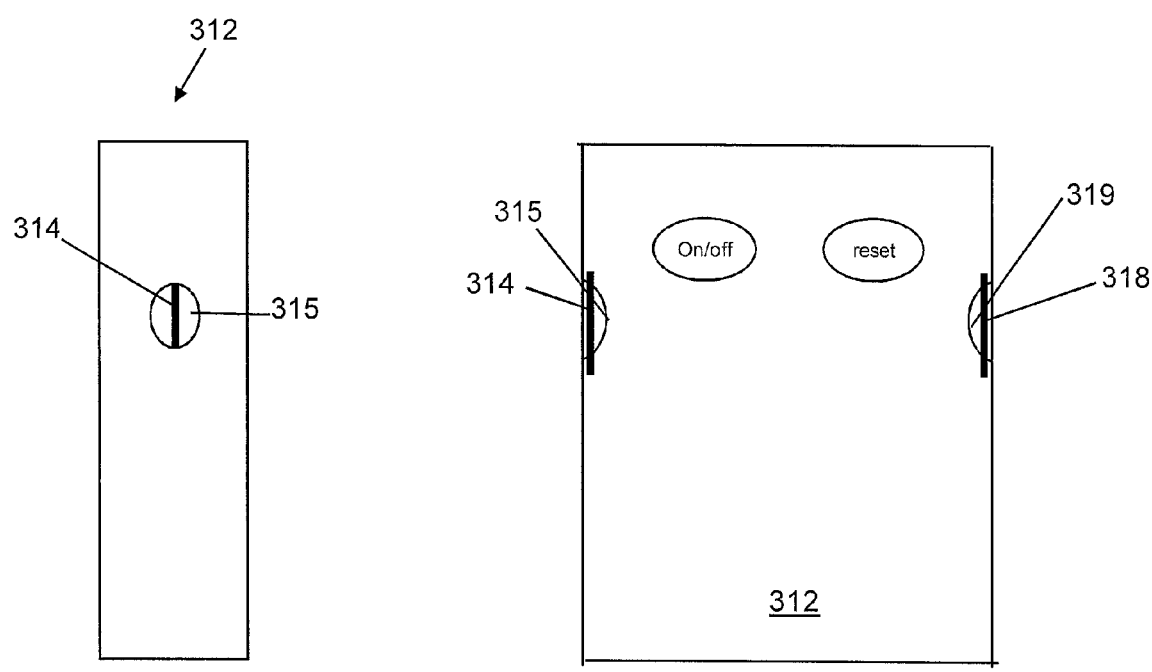
FIG. 9B
FIG. 9C

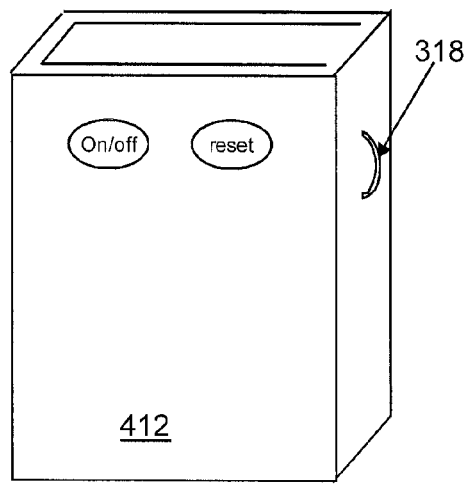
FIG. 10A
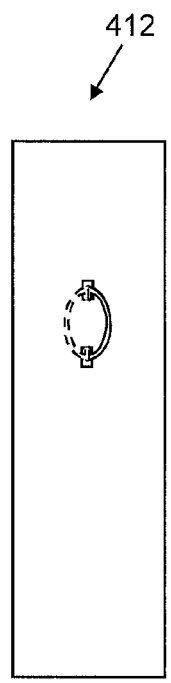
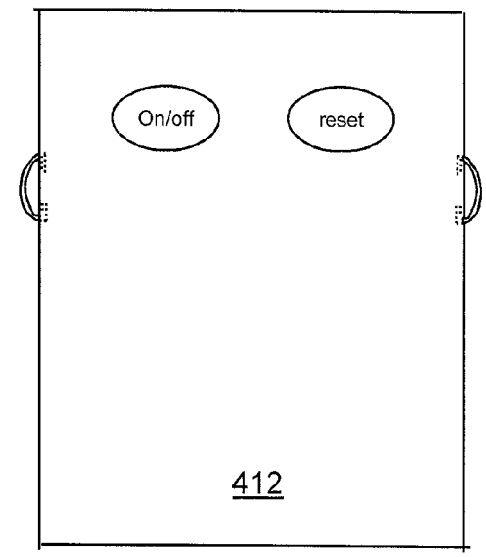
FIG. 10B
FIG. 10C

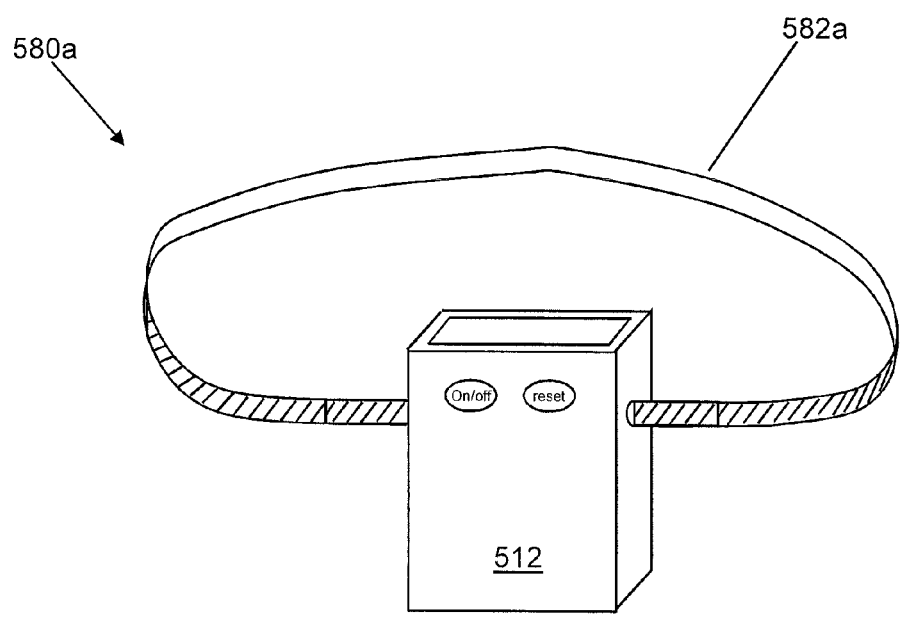
FIG. 11A
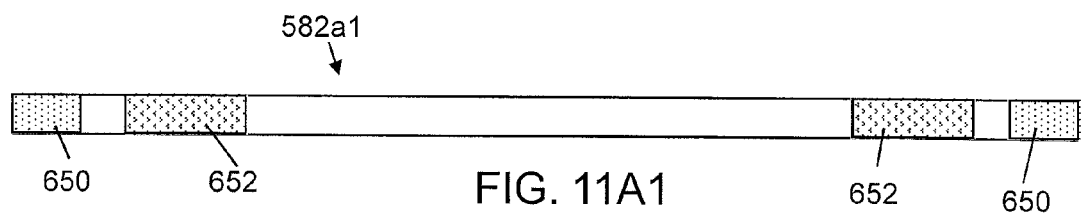
FIG. 11A1
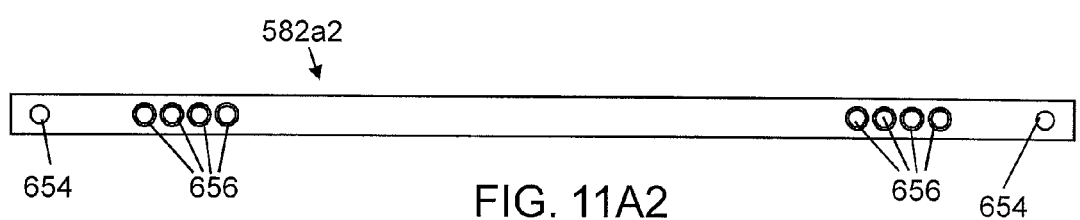
FIG. 11A2

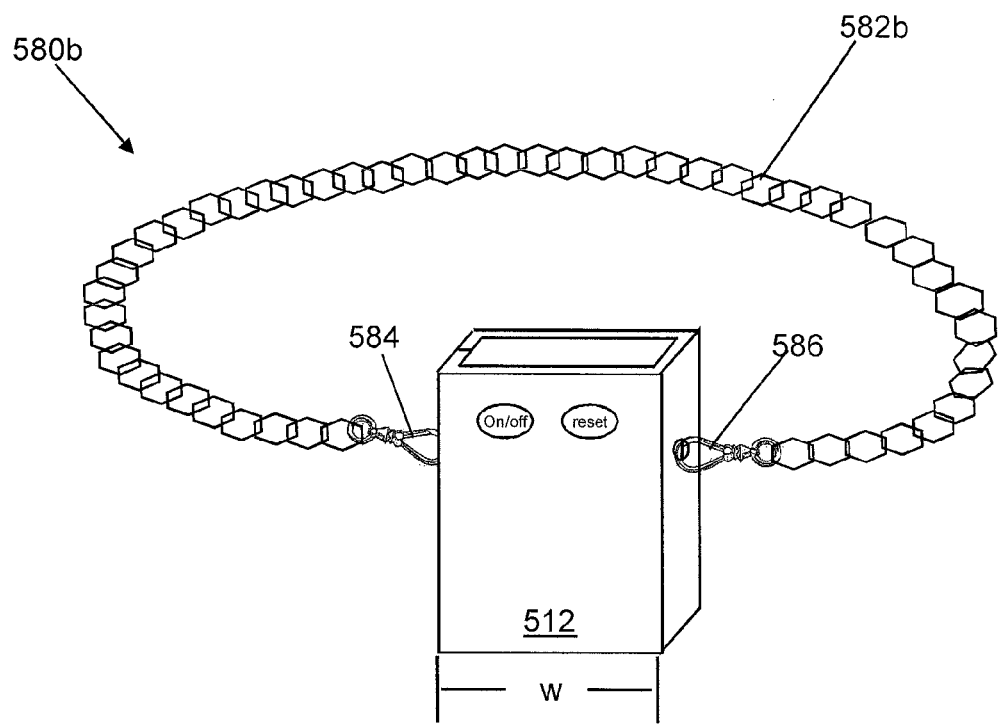
FIG. 11B
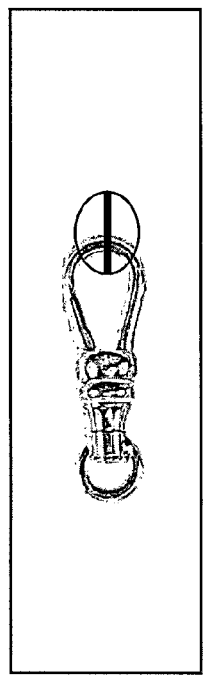
FIG. 11B1
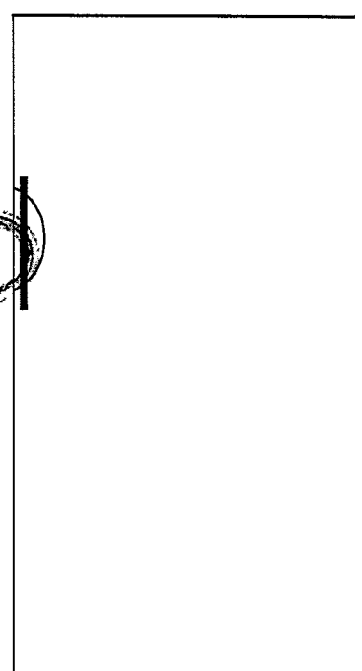
FIG. 11B2

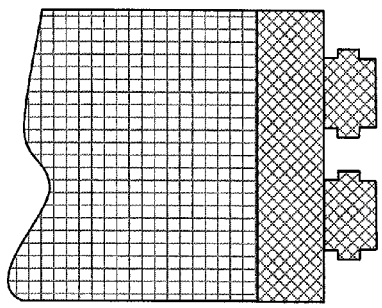
FIG. 13C
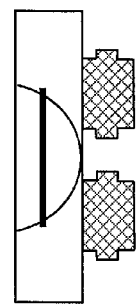
FIG. 13D
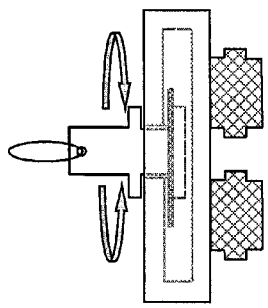
FIG. 13G
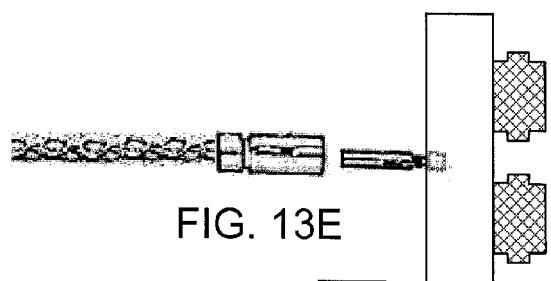
FIG. 13E
FIG. 13F
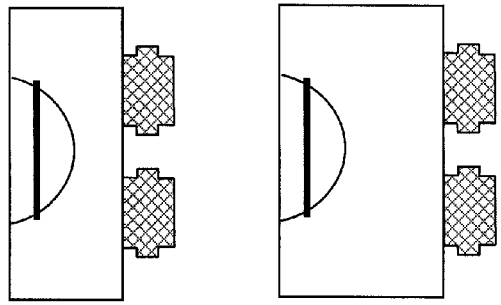
FIG. 13I  FIG. 13J
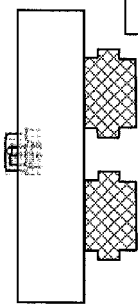
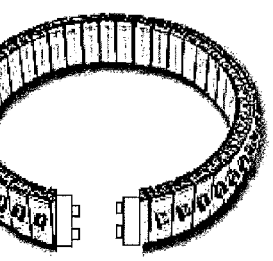
FIG. 13H
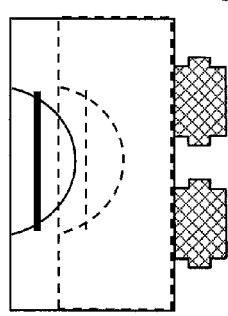
FIG. 13K

WEARABLE FITNESS DEVICE AND FITNESS DEVICE INTERCHANGEABLE WITH PLURAL WEARABLE ARTICLES

RELATED APPLICATIONS

This application is a Continuation of U.S. patent application Ser. No. 12/378,684 filed on Feb. 17, 2009, which is a Continuation in Part of U.S. patent application Ser. No. 11/497,572 filed on Aug. 1, 2006, which claims priority under 35 USC 119 to U.S. Provisional Patent Application No. 60/704,365 filed on Aug. 1, 2005, all of which are incorporated by reference herein.

BACKGROUND OF THE INVENTION

Field of the Invention

The present invention relates to wearable fitness devices and fitness devices interchangeable with plural wearable articles.

Description of Related Art

Fashion played a vital role in the explosion of fitness accessories and the companies which market them, such as Nike, Adidas, Champion, Reebok, and other companies. This industry has brought the gym out onto the street and into the shopping malls, casual restaurants, schools, etc. However, many people still spend the bulk of their time in places where fitness-oriented clothing, no matter how attractive, is not appropriate or desired. The workplace, places of worship, finer dining establishments, concerts and nightclubs, etc. are all venues where fitness apparel is not usually worn. People who spend the majority of their hours outside of the gym are looking for solutions to the problem of building fitness into their lives.

Meanwhile, affordable and attractive fashions and fashion accessories continue to serve busy people's lives. With disposable income higher than disposable time, people look to manufacturers to provide functional attractive solutions. The market for fashion accessories continues to grow.

Certain people attempt to incorporate fitness into their everyday lives. For example, we all know that we should walk more, but tracking our progress has been limited by ugly, impractical step meters. For women and certain workers required to wear uniforms, existing step counters are impractical. Existing counters typically are clipped to the waistband of the wearer's clothing, or alternatively may be strapped to the waist using a band. While this method of attachment is practical when the wearer is dressed in athletic clothing such as jogging pants, shorts or sweat pants, it is impractical and cumbersome when the wearer is dressed in less casual clothing such as a dress, suit or uniform. Many articles of clothing, e.g., dresses, offer no waistband on which the device can be attached, while other articles of clothing, e.g., skirts or dress pants, develop awkward and uncomfortable bulges when the device is attached. For workers in uniform, e.g., wait staff, nurses, etc., attachable devices are outside of the safe or desired dress code. In all circumstances, the clip may be dislodged resulting in loss of the device during normal daily activities such as working, driving, cleaning, using the toilet, etc.

Recent medical research[1] confirms that calories expended outside of planned exercise are critical to maintaining or losing weight. It is generally agreed[2] that the best way for a sedentary (or active) person to increase the amount of calories expended is by simply walking. The government[3] recommends that the general public strive to add extra steps of walking to their daily regimen every day, and to use a step counter or pedometer to measure progress to the attainment of the goal. None-the-less, for many people the inability to accurately capture non-planned exercise steps due to the impracticality of the pedometers available results in frustration, so that the programs goals are not achieved.

[1] www.mayoclinic.org/news2004-mchi/2310.html
[2] See, e.g., www.americaonthemove.org, aom.americaonthemove.org/site/c.hiJRKOPFJpH/b.1311167/k.8725/active_living.htm
[3] CDC, e.g., Wilson D B, Porter J S, Parker G, Smith T J, Kilpatrick J. Using exercise for risk reduction in African American breast cancer survivors: a community-based pilot study [abstract]. Prev Chronic Dis [serial online] 2004 April [date cited]. Available from www.cdc.gov/pcd/issues/2004/apr/03_0034r.htm.; NIH, e.g., http://dnrc.nih.gov/move/pedometer_use.htm Various types of pedometers are known. In general, most pedometers count steps taken due to the impact of every forward or downward movement, which causes a hammer to hit a sensor which activates a counter. Certain pedometers have various sensitivity adjustments to fit individual needs. Some pedometers take the number of steps counted and convert them into a distance. Most pedometers have a tiny spring-set horizontal arm that moves up and down as you walk and measures the vertical movement, e.g., of your legs. Electronic pedometers can detect the impact of your foot hitting the ground. Discussions of pedometers can be found, for example, at *WellSpring*, "Watch Your Step: Pedometers and Physical Activity", Winter 2003 Volume 14, Number 2 by Marshall et al.[4] and *Detroit Free Press* Business News, "Consumer guide: Pedometers", May 4, 2003 by Barbara Arrigo[5].

[4] www.centre4activeliving.ca/publications/wellspring/2003/Spring/HowTheyWork.html
[5] www.freep.com/money/business/guide4_20030504.htm; www.jsonline.com/story/index.aspx?id=144671 (Jun. 1, 2003 editions of the Milwaukee Journal Sentinel)

In addition, accelerometers have been taught as having application in pedometers. For example, U.S. Pat. No. 7,008,350 to Yamazaki, et al. issued Mar. 7, 2006 entitled "Health amount-of-exercise managing device" teaches an apparatus for managing the quantity of exercising to be healthy, using a body fat meter along with a pedometer or an accelerometer for measuring vertical shaky movement; U.S. Pat. No. 6,898,550 to Blackadar, et al. issued May 24, 2005 entitled "Monitoring activity of a user in locomotion on foot" discloses a foot mounted sensor for sensing motion of one's feet such as a solid-state accelerometer that senses acceleration along an acceleration sensing axis; and U.S. Pat. No. 6,298,314 to Blackadar, et al. issued Oct. 2, 2001 entitled "Detecting the starting and stopping of movement of a person on foot" also discloses an accelerometer is mounted on a person's foot so that it generates a signal when the person's foot moves. These various devices advantageously utilize multiple functions of motion-sensing chip technology to incorporate various functionality into the device. Darley U.S. Pat. No. 6,560,903, entitled "Ambulatory Foot Pod," discloses a holder for wearing upon a shoe, which is mentioned as being able to hold a pedometer. Importantly, the disclosure of Darley does not describe in any way how a user would wear the device other than being tightly attached to the shoelaces of a user's shoe or sneaker with an elastic member. While the specification of Darley makes certain broad statements about its applicability to being worn by a person, there is nothing therein that actually describes how the article is worn by a person. However, this is not enabling, because the elastic member described in Darley is only set forth as applicable to tightly attaching to shoelaces, and not for attachment to a limb of a person. As described by Darley, "the retaining member 108" on the object is "capable of receiving an elastic member 110 (or an extension thereof such as a hook or ring) after the elastic member 110 has been stretched about the portion of the object to which the apparatus 100 is to be secured (e.g., crossings 302 of a shoelace 312 of the shoe 304). In the example shown, the retaining member 108 forms a shoulder 202 (see FIG. 2 of Darley) on which a portion 204 of the elastic member 110 can be retained when the elastic member 110 is stretched about the shoelace crossings 302." (Col. 3, lines 7-29). The properties of the elastic member are also described as having sufficient elasticity that at least some tension remains in the elastic member when it is wrapped about the object to which the housing is secured, and examples are provides as "an elastic shock cord such as the type used for hair braids, a rubber stretch cord, or any other cord or element made of a material having the desired characteristics." (Darley, col. 3, lines 33-49). This is indeed consistent with the only operable embodiments described in Darley, namely, to retain the apparatus 100 by securing it about the shoelace crossings 302, and is not consistent with the broad statements about its applicability to being worn by a person about one's wrist, ankle or neck. Since this elastic member is described as an elastic member for tightening to shoelaces, with the requisite elasticity, this certainly would be an uncomfortable, if not dangerous situation, for a wearer to wear directly upon one's body. This is not addressed at all by Darley.

Freeman et al. U.S. Pat. No. 7,229,385, entitled "Wearable Device," discloses a flexible electronic device including a display that is incorporated in an article of clothing or a strap that can be worn. While this reference discloses that the device can be removed from the wearer's body and used as a standalone device, such as a remote control, a display or other electronic device, the entire wearable article is removed (except in one embodiment, where a holographic layer is described as being removable). This is necessary, as electronic circuitry is integral within the article of clothing or strap that the user wears.

In addition to the functional changes required to ensure that the pedometer or accelerometer accurately records the number of steps, it is also desired that the device fit into the wardrobe of the wearer. Darley attempts to address this problem, but only insomuch as the pedometer may be worn directly upon one's shoe. For specific athletic wear, such as when one sets forth to go to a track to walk or run, this may be suitable. However, for most everyday activities in places where fitness-oriented clothing is not appropriate or desired, such as the workplace, places or worship, finer dining establishments, concerts, nightclubs, and shopping venues, many people feel more comfortable wearing clothing that is more formal. Therefore, Darley and other art that addresses incorporation of pedometers specifically in fitness apparel such as athletic shows clearly does not solve this problem. In addition, Darley does not address interchangeability of the same fitness device with different articles of clothing to coordinate with a wearer's outfit or to accommodate one's personal taste.

Furthermore, the device of Freeman et al. is specifically an electronic device, and makes no attempt to provide a device that coordinates with one's outfit or accommodate personal tastes. In addition, Freeman et al. does not address interchangeability of the same fitness device with different articles of clothing.

Accordingly, these problems that are not addressed by existing wearable articles are solved by various embodiments of the present invention, integrating functionality and fashion to enhance the success of a wearer using the product and following the guidelines for healthy living as medical experts recommend. While the benefits of pedometers and the like are well known, heretofore unknown to the art are integrated fashionable accessories and garments suitable for holding pedometers and/or other fitness devices.

SUMMARY OF THE INVENTION

Therefore, it is an object of the invention to provide desirable fashion accessories with functional fitness devices, such as pedometers or accelerometers, thereby allowing one to track their steps while at work, shopping, an evening out, or anytime one is on the move.

The present invention relates to wearable fitness device and fitness device interchangeable with plural wearable articles.

In certain embodiments, the wearable fitness device includes a wearable article having a structure therein or thereon configured and dimensioned for holding a fitness device such as a pedometer in an oriented position.

Fashion accessories with functional fitness device are described, thereby allowing one to track their steps while at work, shopping, an evening out, or anytime one is on the move. Further, a fitness device is provided that can capture steps practically and comfortably during a normal person's daily routine.

BRIEF DESCRIPTION OF THE FIGURES

The foregoing summary as well as the following detailed description of preferred embodiments of the invention will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, where:

FIG. 1 shows a general embodiment of a system of the present invention wherein a fitness device may be interchangeable between multiple types of wearable articles;

FIGS. 2A and 2B shows an embodiment of a wearable article for positioning and orienting a fitness device;

FIG. 7C is a top view of the wearable fitness device of FIG. 7A depicted without the wearable article;

FIG. 7D is a side view of the fitness device of FIG. 7A depicted without the wearable article;

FIG. 7E is a side perspective exploded view of the fitness device of FIG. 7A, without the wearable article;

FIG. 7F is an enlarged section view of an embodiment of the swivel connector of the fitness device of FIG. 7A;

FIG. 9A is a front perspective view of a fitness device according to another embodiment;

FIG. 9B is a side view of the fitness device of FIG. 9A;

FIG. 9C is a front view of the fitness device of FIG. 9A;

FIG. 10A is a front perspective view of a fitness device according to another embodiment;

FIG. 10B is a side view of the fitness device of FIG. 10A;

FIG. 10C is a front view of the fitness device of FIG. 10A;

FIG. 11A shows another embodiment of a wearable fitness device;

FIGS. 11A1 and 11A2 show embodiments of straps that attach as shown in FIG. 11A;

FIG. 11B shows a further embodiment of a wearable fitness device;

FIG. 11B1 shows a side view of the wearable fitness device shown in the embodiment of FIG. 11B;

FIG. 11B2 shows an enlarged front view of a portion of the wearable fitness device shown in the embodiment of FIG. 11B;

FIGS. 13C-13K show various types of sockets for use in the embodiment of FIGS. 13A and 13B;

DETAILED DESCRIPTION OF THE INVENTION

Figure 4A:
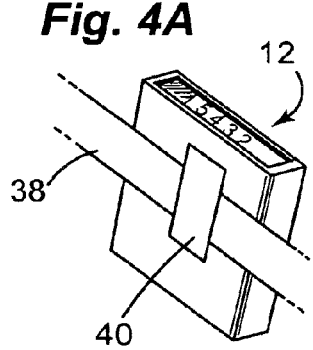
FIGS. 4A-4C show exemplary structures for positioning and orienting a fitness device on a wearable article.

Provided herein is a fitness accessory in the form of a wearable article of clothing and a fitness device attached to the wearable article of clothing. In certain embodiments, a fitness accessory in the form of a wearable article of clothing includes a device requiring accurate positioning and orientation such as a pedometer.

Referring to FIG. 1, a general system 10 of the present invention is shown, wherein a fitness device 12, the fitness device including those used to measure one's distance traversed such as a pedometer (e.g., a mechanical pedometer, an electro-mechanical pedometer, an electronic pedometer) or an accelerometer, is depicted as being associated with plural types of articles of clothing or fashion accessories. For example, anklets 14 and 16, belt 18, shorts 20, or a bandanna 22 (or other type of garment suitable for tying around one's body or limb, e.g., armband) may be interchangeable with a fitness device 12 in the system or kit 10 according to certain aspects of the present invention. Note that additionally, the fitness device 12 may be interchangeable with other wearable articles, for example, of the same type (e.g., anklets, shorts, bandana, armband, belt, etc.) of different style or color, for example, to coordinate with different color outfits and/or accessories.

As shown, the belt 18 has an extended shape configured to fit within a buckle, and associated holes as in conventional belts. In certain preferred embodiments, the belt 18 is an adjustable band. A suitable holding structure is included for holding the fitness device 12. Alternatively, the belt 18 could use a hook and loop fastening system, one or more buttons, snap-fit fasteners, a peg and hole mechanism, chain links, elastic materials, or any other suitable fastening system.

Anklet 14 is configured, e.g., as a slide-on type anklet. Preferably, the anklet is formed of a suitable shape and material for a core that maintains its position upon one's body. A suitable holding structure is included for holding the fitness device 12. In certain embodiments, an anklet 14 is formed of links, beads, or rope chain, In other embodiment, an anklet 14 or a core thereof is formed of a suitable elastic material such as spandex fiber, knitted elastics, net elastics, rubber-based articles or stretchable cloth. Further, the anklet 14 may be formed of a suitable elastic configuration, such as a loose cloth encompassing an elastic strap as the core. Alternatively, the anklet 14 may include a suitable spring as the core. Such material desirably provides a suitably snug fit to prevent the anklet from sliding out of position and maintain suitable orientation, while not being excessively tight to harm the wearer. Harm to the wearer to be avoided includes irritation to the limb, and/or reduced blood circulation to the limb.

Anklet 16 is in the form, e.g., of a chain link anklet. A suitable holding structure is included for holding the fitness device 12. Connections between the fitness device 12 and the anklet 16 include, for example, suitable clasps (e.g., lobster claw clasps) on each end of an anklet, with connector rings attached to each side of the fitness device 12.

Other types of anklets, armbands, belts or other wearable articles may also be used and integrated with the system 10, including those secured in place using an adjustable band. Suitable adjustable bands include those with a buckle and associated holes, a hook and loop fastening system, one or more buttons, snap-fit fasteners, a peg and hole mechanism, chain links, or any other suitable fastening system. The article of clothing may include anklets, belts, pants/shorts, as shown with respect to FIG. 1, or shirts/blouses, undergarments, shoes, or other articles of clothing.

Referring to FIG. 2A, a wearable article 24 includes a fitness device 12 associated therewith. In general, the wearable article 24 includes a strap 26, e.g., forming the body of the article 24. The strap 26 can secure the article 24 around a person's ankle, leg, or waist, or wrist. In certain embodiments, the article 24 incorporates the fitness device 12 in accurate positioning and orientation to function effectively.

In the example of FIG. 2A, the article 24 includes a pocket or holding structure 28 permanently or removably attached thereto. The pocket is generally characterized by a front panel 30 width w' and a sidewall 32 giving the pocket 28 a depth d'. In certain preferred embodiments, the fitness device 12 has correspondingly similar width w" and depth d" so that the fitness device 12 may be securely held within the pocket 28. FIG. 2B shows the fitness device 12 being inserted 34 within the pocket 28 of the wearable article 24.

Figure 3:
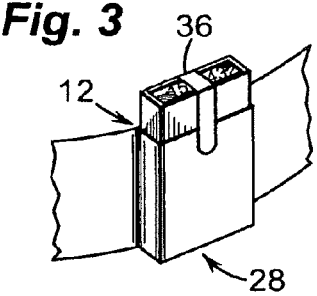
FIG. 3 shows an exemplary pocket with a securing strap for holding a fitness device.

Referring now to FIG. 3, a fitness device 12 is shown within a pocket 28 further including a securing strap 36. The securing strap 36 serves to hold the fitness device 12 in position, prevent accidental removal of the fitness device 12, provide orienting functionality, or a combination of the above features. The securing strap 36 may attach to the front panel of the pocket 28 as shown, or alternatively attach to another suitable location. The securing strap 36 may secure to the front panel or other suitable location by any type of removable attachment including but not limited to a hook and loop fastening system, a buckle, one or more buttons, snap-fit fasteners, a peg and hole mechanism, chain links, or any other suitable fastening system. Further, the strap may be formed of a flexible material such as cloth, webbing, leather, natural fibers, flexible plastic, or other suitable material. Alternatively may be formed of a rigid or semi-rigid material with a suitable hinge structure.

The fitness device 12 may be attached to the wearable article with a variety of structures. Preferably, in the case of certain pedometers as the fitness device 12, the structures allow the fitness device 12 to be maintained in a proper position on one's body to accurately measure ones' walking and/or running steps. For example, pedometers requiring maintenance of proper orientation during use to accurately measure one's steps desirably are attached to the wearable article in a manner that facilitates such proper orientation.

Referring to FIG. 4A, the fitness device 12 may be attached to an article or portion of an article 38 by threading the elongated article 38 through a loop 40.

Figure 4B:
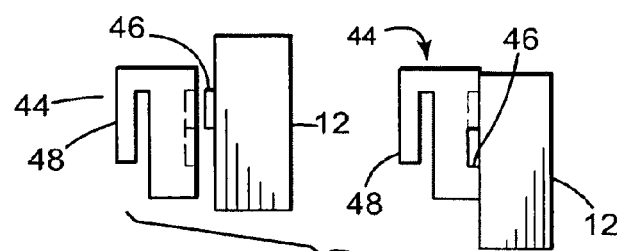

Referring to FIG. 4B, the fitness device 12 may be attached to a clip structure 44. Clip structure 44 is configured for holding the fitness device 12. As shown, the clip structure 44 includes a receiving portion corresponding to a suitable protrusion 46 of the fitness device 12. The clip structure 44 further includes a suitable structure 48 for attaching to an article of clothing on one's body, e.g., a slide clip structure. Alternatively, the clip 44 may include a protrusion associated with a suitable receiving portion on the fitness device 12. Other removable attachment structures may be used to attach the fitness device 12 to the clip structure 44.

Figure 4C:
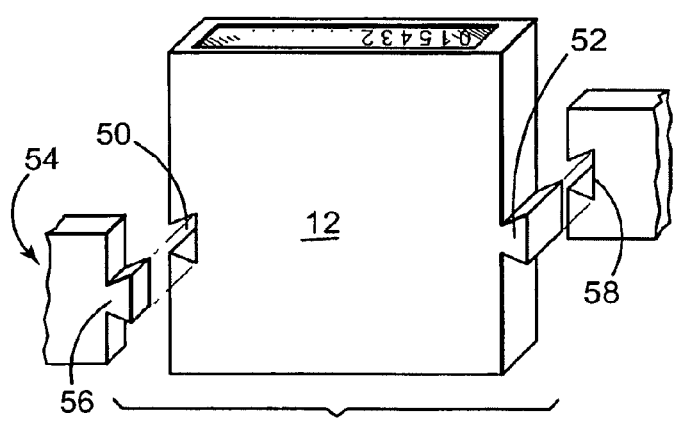

Referring now to FIG. 4C, another example of a suitable removably connected configuration for holding the fitness device 12 in place is shown. The fitness device 12 includes suitable features 50, 52 corresponding to mating features 56, 58 on a wearable article 54 (or a portion thereof). While the removably connected configuration is shown as having male portion 56 of article 54 secured to female portion 50 of fitness device 12, and as having female portion 58 of article 54 secured to male portion 52 of fitness device 12, it will be appreciated that other configurations are possible. The features 50, 52, 56, 58 may be snap fit, friction fit, or other suitable removable connection structures. A key benefit of the system of FIG. 4C is that it per se provides a one-way connection between the fashion portion and the fitness device, which allows for only possible orientation upon attachment.

Figure 5:
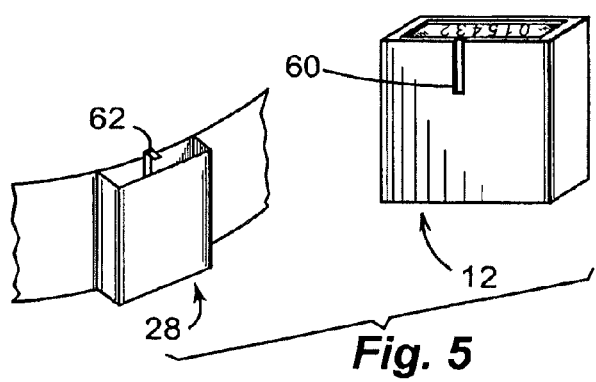
FIG. 5 shows an exemplary system for properly aligning a fitness device on a wearable article.

Referring now to FIG. 5, an example of an orienting feature is shown. Fitness device 12 includes an alignment mark 60. A pocket 28 (or other suitable holder) includes a corresponding alignment mark 62. Preferably, the alignment marks are in such a position to minimize or eliminate improper orientation of the fitness device.

Figure 6:
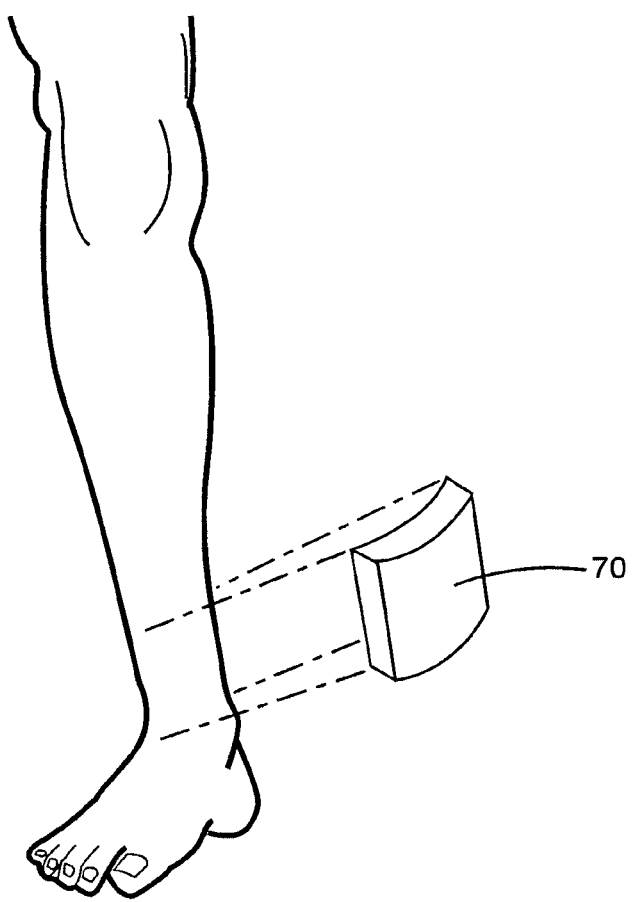
FIG. 6 shows an exemplary embodiment of a fitness device including an added degree of comfort provided by matching the shape of a wearer's body or leg.

Referring now to FIG. 6, another feature of the present invention is provided to enhance comfort. A fitness device 70 is provided having suitable curvature, e.g., of molded plastic, to fit comfortably against one's body. The curvature can be any suitable shape of curvature and degree of curvature, depending upon the device and the location at which it will be attached to the body, e.g, leg, arm, neck, torso.

In one embodiment, referring to FIGS. 7A-7D, a wearable fitness device 80 includes a wearable article 82 in the form of a decorative anklet having first and second end connectors 84, 86, whereby the first end connector 84 (e.g., shown in the form of a lobster claw clasp or a caribiner trigger clasp) can be connected to one of rings 88, 90, 92, 94 attached to a fitness device 112 and the second end connector 86 can be connected to one of rings 96, 98, 100, 102 attached to the fitness device 112. In particular, ring 88 is connected to a swivel connector 114 that extends from a side 116 of the fitness device 112, and ring 96 is connected to a swivel connector 118 that extends from a side 120 the fitness device 112.

Figure 7A:
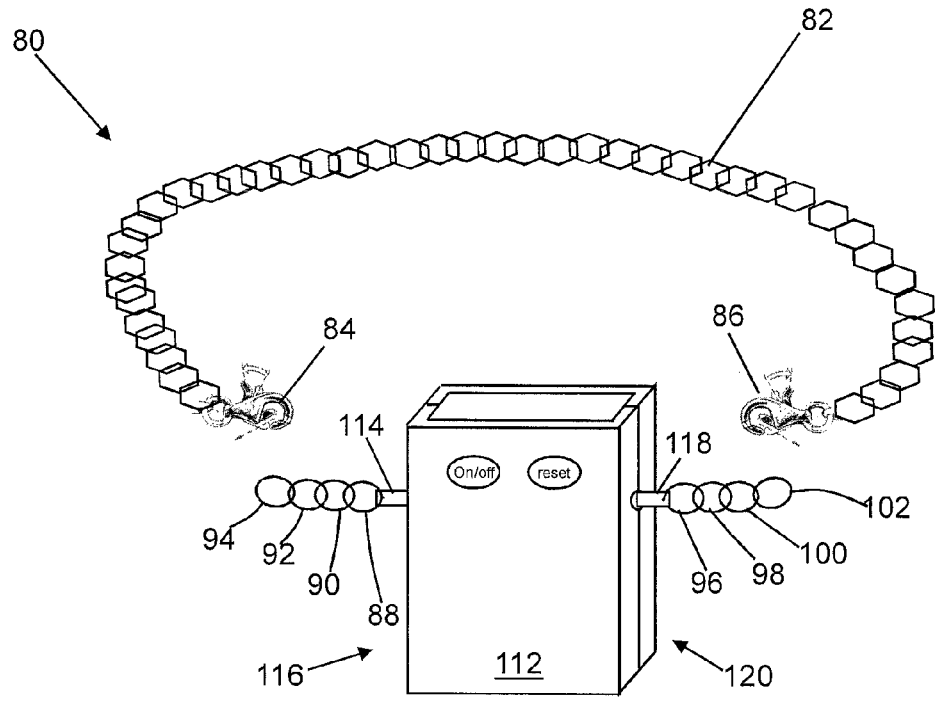
FIG. 7A is a front perspective view of a wearable fitness device according to another embodiment showing a wearable article separate from the fitness device.
Figure 7B:
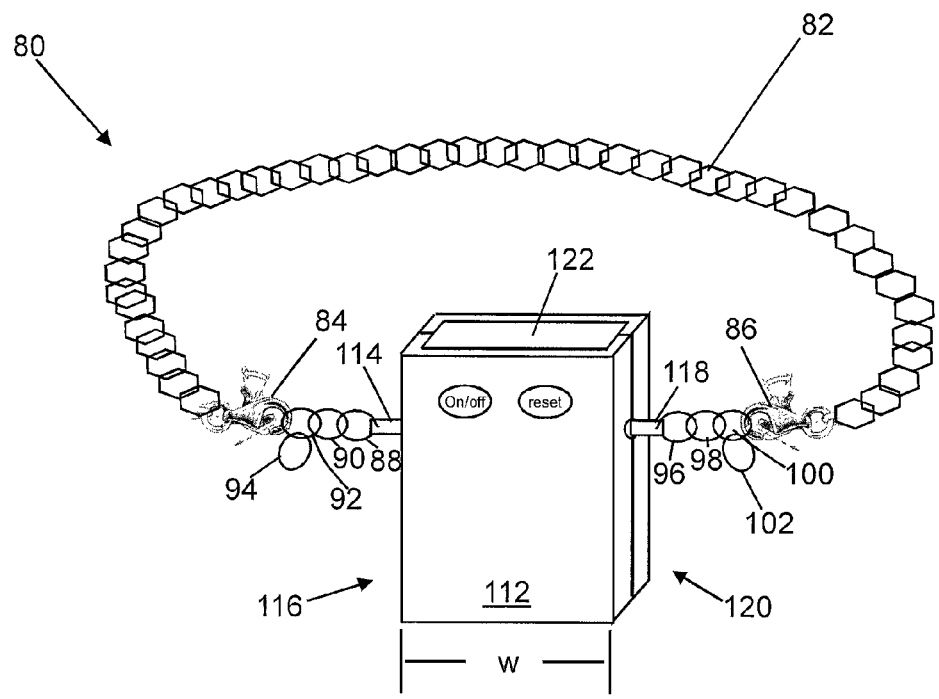
FIG. 7B is a front perspective view of the wearable fitness device of FIG. 7A showing a wearable article adjustably attached to the fitness device.

As shown in FIG. 7B, when the first and second end connectors 84, 86 are connected to one of the rings, the device can be worn on a user, for example, as an anklet. In particular, as shown in FIG. 7B, connector 84 can be attached to ring 92, and connector 86 can be attached to ring 100, thereby providing a overall circumferential dimension of the wearable fitness device 80 of approximately the length of the wearable article 82 plus the width w of the fitness device 112 plus the combined length of extension of the in swivel connectors 114, 118 plus, in the embodiment of FIG. 7B, the combined length of rings 88, 90, 92, 96, 98 and 100. If a larger dimension is needed, the lengths of rings 94 and 102 can be added. If a smaller dimension is required by a user, one or both of connectors 84, 86 can be removably connected one of the rings closer to the swivel connectors 114, 118. Of course, while there are four rings shown on each side, fewer or more can be provided, with the same number or a different number on each side, depending on the desired degree of adjustability.

In a preferred embodiment, as shown in FIGS. 7A-7C, the fitness device 112 includes a display 122 at the top of the device (when worn by a user). This allows the user to easily view the information without removing the device or awkwardly bending or twisting to view the information, such as with a front display device. The information can be provided on the display 122 in either a numerical format, or using indicators (e.g., a bar or circle for every 1000 steps), to allow the user to monitor their cumulative exercise.

In order to facilitate maintaining proper orientation, swivels 114, 118 are positioned above the center of the fitness device 112. Accordingly, due to the positioning, the rotational capabilities of the swivel connectors 114, 118, and the adjustability, when the wearable fitness device 80 is worn as an anklet, for example, so that it rests just above the lateral malleolus, the fitness device is maintained in proper orientation. The orientation allows the display 122 to be visible to the user, and an upright orientation is also important in embodiments where the fitness device 112 is a mechanical or electro-mechanical pedometer.

In one embodiment of the fitness device 112 shown in FIGS. 7A-7D, and referring now to FIGS. 7E and 7F, the swivel connectors 114, 118 are installed in the body of the fitness device 112 during manufacture. The fitness device includes a body having a first section 126 (e.g., on a face of the fitness device 112 having on/off and reset buttons) and a second section 124 (e.g., on a face of the fitness device 112 having a battery access compartment 130 for insertion of a battery 132 to provide electrical power to a mechanism 128 and the display 122 of the fitness device 112, e.g., a pedometer). On each of the sides 116, 120, each section 124, 126 includes cut-away portions 134, 136, 138 and 140 (portion 140 shown in broken lines), for instance, in the form of semicircles. As shown in detail in FIG. 7F, where a section of one of the sides of the fitness device 112 is shown, the swivel connector 114 includes a distal cross member 142 having an internal stem 144 extending therefrom with a shoulder 146, and an external stem 147 extending from the shoulder with an aperture 148 therethrough. The internal stem is generally cylindrical having a diameter slightly smaller than the diameter of the circle formed by the semicircular cut-away portions when the sections 124, 126 are joined to form the fitness accessory 112, thereby allowing it to rotate. The distal cross member 142 prevents the swivel connector 114 from pulling away from the side of the fitness device 112, and the shoulder 146 prevents the swivel connector 114 from pushing into the fitness device 112. The ring 88 described with respect to FIGS. 7A-7C is inserted through the aperture 148 and is crimped or soldered in place to prevent detachment. The same structure can be used for the other swivel connector 118.

Figure 8A:
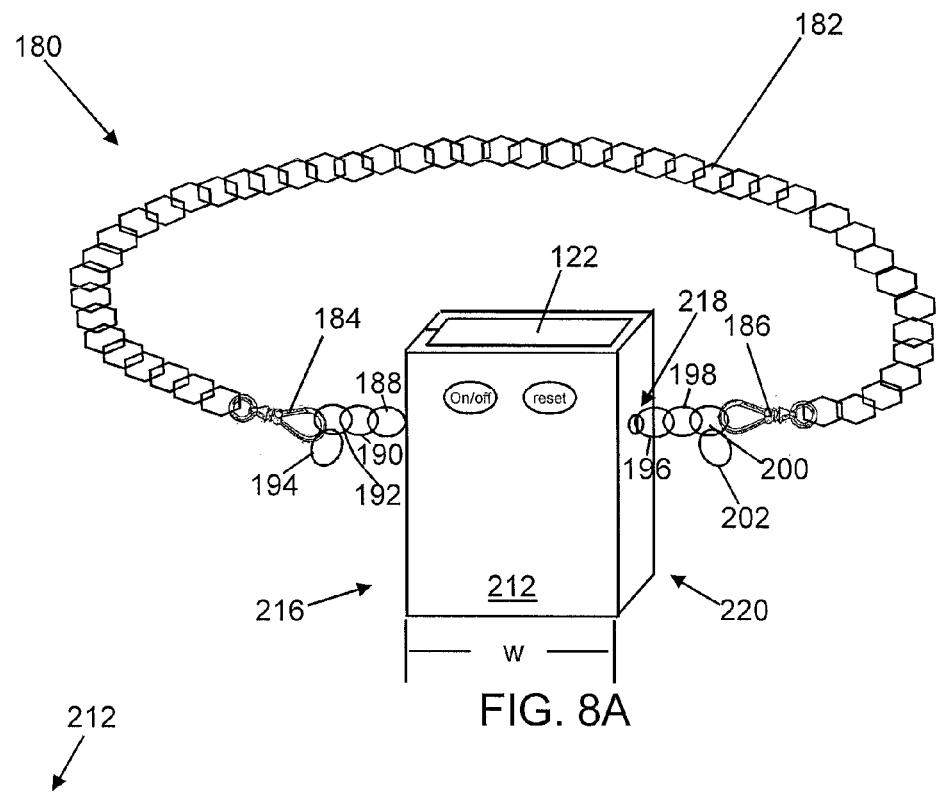
FIG. 8A is a front perspective view of a wearable fitness device according to a further embodiment showing a wearable article adjustably attached to the fitness device.
Figure 8B:
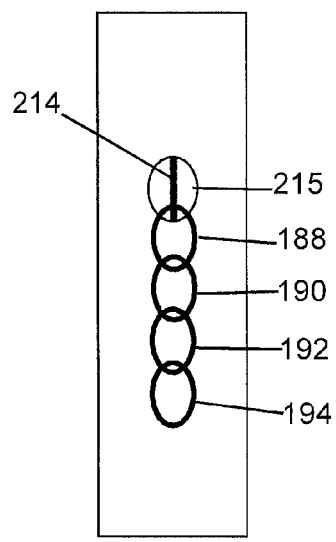
FIG. 8B is a side view of the fitness device of FIG. 8A shown without the wearable article.
Figure 8C:
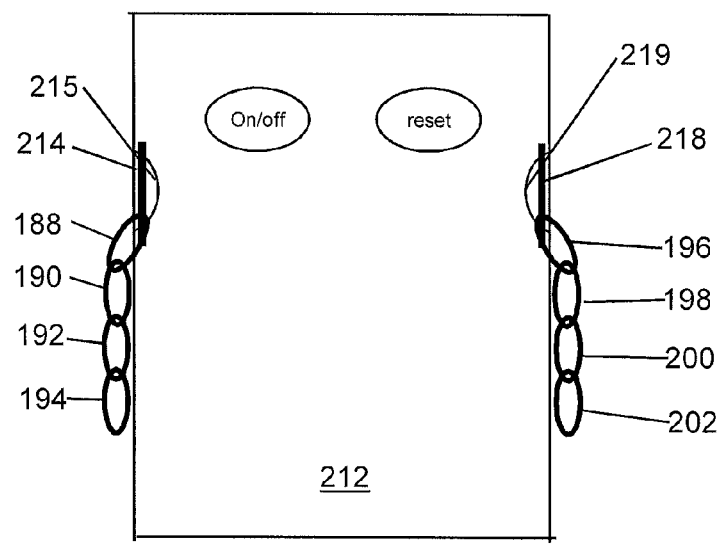
FIG. 8C is a front view of the fitness device of FIG. 8A depicted without the wearable article.

In another embodiment, and referring now to FIGS. 8A-8C, a wearable fitness device 180 includes a wearable article 182 in the form of a decorative anklet having first and second end swivel connectors 184, 186, whereby the first end swivel connector 184 can be connected to one of rings 188, 190, 192, 194 attached to a fitness device 212 (and shown in FIG. 8A as attached to ring 192) and the second end connector 186 can be connected to one of rings 196, 198, 200, 202 attached to the fitness device 212 (and shown in FIG. 8A as attached to ring 200). In particular, ring 188 is connected to an inset bar 214 on a side 216 of the fitness device 212, and ring 196 is connected to an inset bar 218 on a side 220 the fitness device 212. As shown in FIG. 8A, when the first and second end connectors 184, 186 are connected to one of the rings, the device can be worn on a user, for example, as an anklet. In particular, as shown in FIG. 8A, connector 184 can be attached to ring 192, and connector 186 can be attached to ring 200, thereby providing a overall circumferential dimension of the wearable fitness device 180 of approximately the length of the wearable article 182 plus the width w of the fitness device 212 plus, in the embodiment of FIG. 8A, the combined length of rings 188, 190, 192, 196, 198 and 200. If a larger dimension is needed, the lengths of rings 194 and 202 can be added. If a smaller dimension is required by a user, one or both of connectors 184, 186 can be removably connected one of the rings closer to the inset bar 218 and the inset bar 214. Of course, while there are four rings shown on each side, fewer or more can be provided, with the same number or a different number on each side, depending on the desired degree of adjustability. As shown in more detail in FIGS. 8B and 8C, the inset bars 214, 218 are within recesses 215, 219, respectively. The inset bars may be held in place by suitable apertures, for instance, inserted during manufacture of the fitness device 212. Furthermore, the inset bars may be similar to watch band pins, which are spring biased and include ends that slide into suitably dimensioned apertures. While the bars 214, 218 are shown extending vertically, they may also extend horizontally or at any other desired angle. Similar to the embodiment shown with respect to FIGS. 7A-7F, the fitness device 212 includes a display 122 at the top of the device (when worn by a user), thereby allowing the user to easily view the information without removing the device or awkwardly bending or twisting to view the information, such as with a front display device.

In order to facilitate maintaining proper orientation, bars 214, 218 are positioned above the center of the fitness device 112. Accordingly, due to the positioning, the rotational capabilities of the swivel connectors 184, 186, and the adjustability, when the wearable fitness device 180 is worn as an anklet, for example, so that it rests just above the lateral malleolus, the fitness device is maintained in proper orientation. The orientation allows the display 122 to be visible to the user, and an upright orientation is also important in embodiments where the fitness device 212 is a mechanical or electro-mechanical pedometer.

In another embodiment, and referring now to FIGS. 9A-C, a fitness device 312 is shown without the accompanying wearable articles. The fitness device 312 includes, for instance, inset bars 314, 318 on either side of the fitness device 312. These inset bars are positioned in recesses 315, 319, respectively, in a similar manner as the embodiment shown with respect to FIGS. 8A-8C. Similar to the embodiments shown with respect to FIGS. 7A-7E and 8A-8C, the inset bars are positioned above the center of the fitness device to facilitate proper orientation.

In another embodiment, and referring now to FIGS. 10A-C, a fitness device 412 is shown without the accompanying wearable articles. The fitness device 412 includes, for instance, rings 414, 418 attached at the sides of the fitness device 412. These rings 414, 418, which may be semicircular, semi-oval, D-shaped, rectangular, trapezoidal, or other suitable shape, are inset within the housing of the fitness device 412 (e.g., as shown with dotted lines in FIG. 10C) so as to swivel between two positions against the side edge of the housing of the fitness device 412 (e.g., as shown with dashed lines in FIG. 10B). Similar to the embodiments shown with respect to FIGS. 7A-7E and 8A-8C, the inset bars are positioned above the center of the fitness device to facilitate proper orientation.

Referring now to FIGS. 11A and 11B, embodiments of wearable articles attached to the fitness devices of either FIGS. 9A-9C or 10A-10C are shown. FIG. 11A shows a fitness device 580a including a wearable article 582a in the form of a strap that attaches to the connection structures of the fitness devices of either FIGS. 9A-9C or 10A-10C. The strap 582a is configured to wrap around either the inset bars 314, 318 of the fitness device 312, or through the rings 414, 418 of the fitness device 412. FIG. 11A1 shows a strap 582a1 having hook fasteners and loop fasteners 650 on either side that mate together for an adjustable fit. FIG. 11A2 shows a strap 582a1 having a snap button 654 and a series of snap button receptacles 656 on either side that mate together for an adjustable fit. The strap or a core thereof can be formed of a suitable elastic material such as spandex fiber, knitted elastics, net elastics, rubber-based articles or stretchable cloth. Further, the strap may be formed of a suitable elastic configuration, such as a loose cloth encompassing an elastic strap as the core. Alternatively, the strap may include a suitable spring as the core. Such material desirably provides a suitably snug fit to prevent the strap from sliding out of position, while not being excessively tight to harm the wearer by reducing blood circulation or causing irritation.

FIG. 11B shows a fitness device 580b including a wearable article 582b in the form of a chain (e.g., an anklet) that includes connectors 584, 586 that attaches to the connection structures of the fitness devices of either FIGS. 9A-9C or 10A-10C. FIGS. 11B1 and 11B2 show a side view and a front view (a portion thereof) of fitness device 512 with the connector embodiment of FIGS. 9A-9C. Notably, the connectors of either FIGS. 9A-9C or 10A-10C can accommodate either a strap as shown in FIG. 11A, or a chain as shown in FIG. 11B. Therefore, a kit may be provided that allows a user to change between one or more style straps and one or more style chains with ease, while utilizing the same fitness device 512.

Figure 12A:
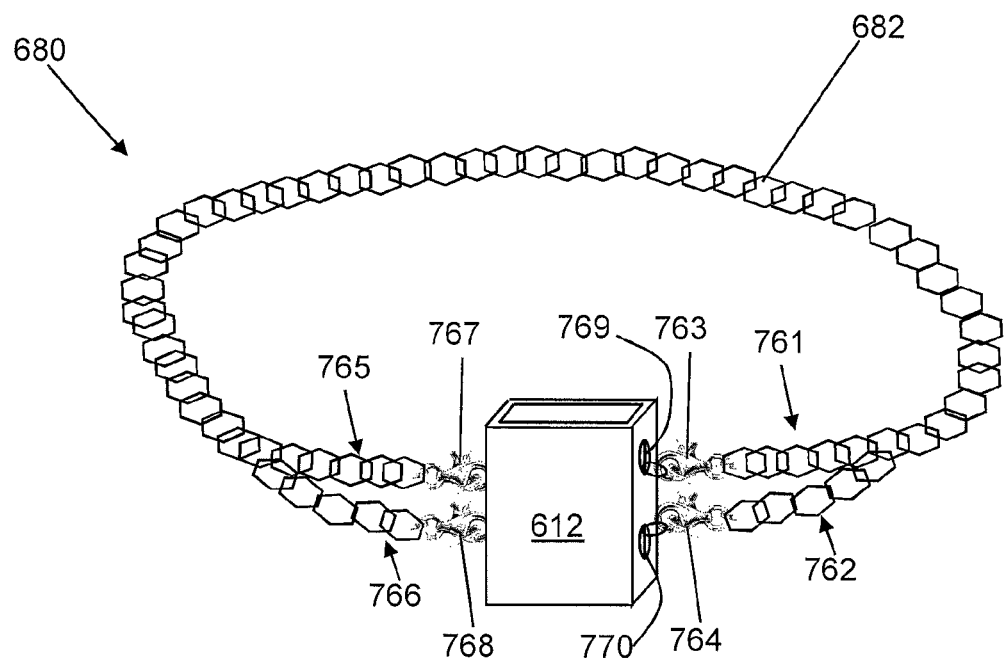
FIGS. 12A and 12B show alternative embodiments of connections structures of a wearable fitness device.

Referring now to FIG. 12A, another embodiment of a wearable fitness device 680 is shown, where the configuration of a wearable article 682 and the fitness device 612 includes features to maintain orientation during use. In this embodiment, the wearable article 682, for instance in the form of an anklet, includes two sets of links 761, 762 with distal connectors 763, 764 at a first end and two sets of links 765, 766 with distal connectors 767, 768 at the second end. The connectors 763, 764 attach to the fitness device 612, for instance, via two sets of inset bars 769, 770 on the first side of the device 612, and the connectors 767, 768 attach to inset bars (not shown) on the second side. As an alternative to inset bars, one or more rings may extend from the sides of the fitness device, for instance, as shown in FIGS. 7A-7E, 8A-8C or 10A-10C. This configuration, by spreading the connection points, allows the fitness device 612 to be maintained in proper orientation for ease of viewing of the display and/or for operation of the fitness device, e.g., in the case of an electro-mechanical or mechanical pedometer. Furthermore, in order to maintain proper orientation, the swivel connectors are optional in this embodiment.

Figure 12B:
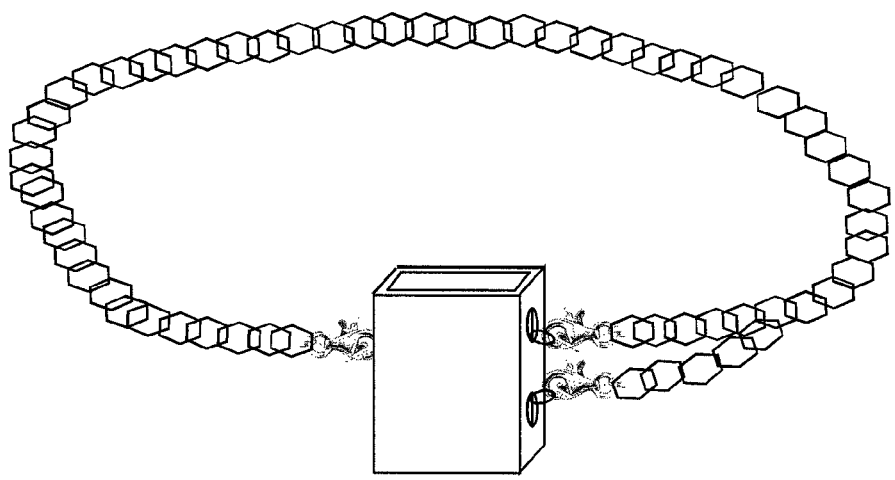

In another embodiment, and referring now to FIG. 12B, only one side of a fitness device includes a pair of inset bars (or extended rings, or the like) and one corresponding end of the wearable article includes branched links and associated connectors.

Figures 13A, 13B:
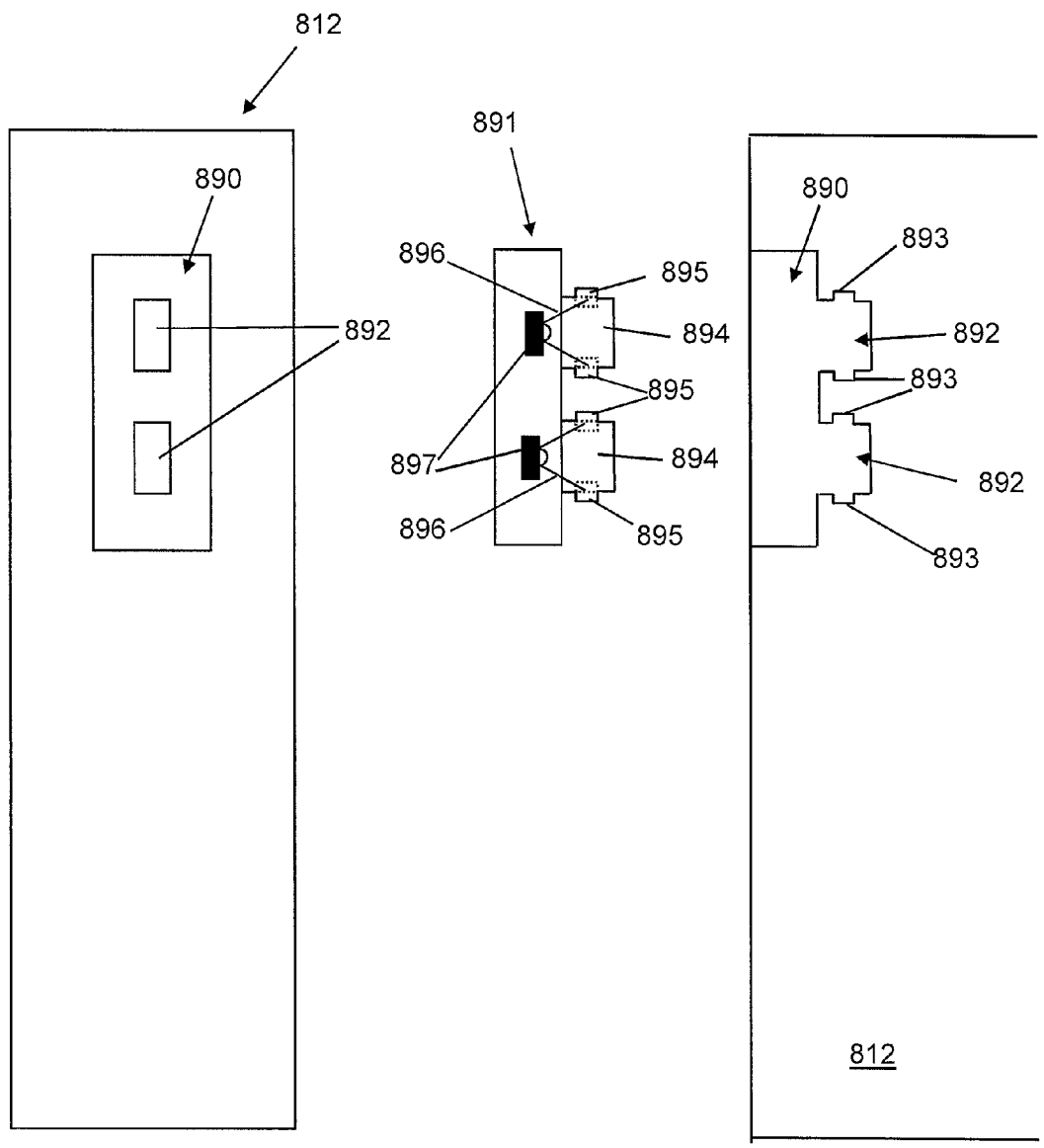
FIGS. 13A and 13B show side and front portion views, respectively, of a further embodiment of a wearable fitness device including a modular connections structure socket and receptacle.

Referring now to FIGS. 13A-13B, in further embodiments a fitness device 812 may be provided with a receptacle 890 for receiving a socket connector 891. Receptacle 890 includes, for instance, insets 892 including notches 893. Socket connector 892 includes corresponding extension portions 894 with spring biased tabs 895, for instance, biased by a V-shaped torsion spring 896 internal to the socket connector 892 and mechanically cooperating with an actuator 897 on the outside of the socket 892. Other configurations of biasing members may be used to lock the socket 891 within the receptacle 890.

As shown in FIG. 13B, the socket connector 891 does not depict any attachment structures for receiving connectors as described elsewhere herein. However, with continuing reference to FIGS. 13A and 13B, the socket connector 891 may take various forms, and a plurality of socket connectors as shown in FIGS. 13C-13H, and various embodiments of socket connectors and wearable articles attached thereto may be provided in a kit comprising the fitness device 812 as well as a plurality of wearable articles.

FIG. 13C shows a socket connector having a strap integral therewith, for instance, to provide on both ends of a strap. FIG. 13D shows an inset bar socket, for instance, capable of receiving a jewelry finding such as a trigger clasp or other suitable type of clasp, or a strap as shown and described with respect to FIG. 11A. FIG. 13E shows a socket having a male end of a barrel clasp, and a portion of a chain (i.e., wearable article) having a corresponding female portion of a barrel clasp. FIG. 13F shows a socket having on portion of a magnetic clasp (i.e., either a ferrous material or a magnetic material), and a portion of a chain (i.e., wearable article) having a corresponding portion of a magnetic clasp (opposite the portion in the socket). In the embodiments of FIGS. 13E and 13F, the portion of the clasp integral with the socket may be, for instance, directly molded in the socket, integrally cast (in the case of metal or plastic clasp portions), or soldered to the socket.

FIG. 13G shows a swivel connector, shown with one ring attached (although more than one ring may be attached, or the aperture receiving the ring may be large enough to directly connect with a connecting structure on the ends of the wearable article. FIG. 13H shows an expansion type anklet, having socket connectors on either end. Next, with reference to FIGS. 13I and 13J, socket connectors may provide various length extensions to accommodate different sizes of a wearer and ensure proper fit and orientation. In addition, size variation can be accomplished by a telescoping socket, for instance, as schematically depicted in FIG. 13K.

Figure 14A:
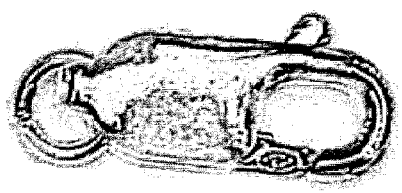
FIGS. 14A-14J show various types of claps that can be used with certain embodiments of the wearable fitness device of the present invention.
Figure 14B:
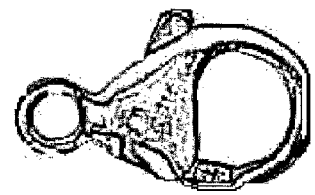
Figure 14C:
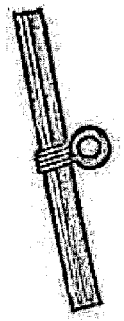
Figure 14D:
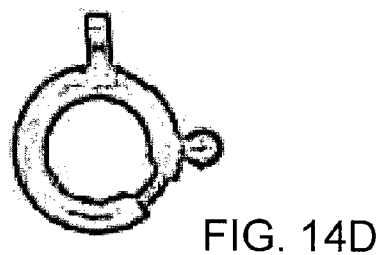
Figure 14F:
Figure 14E:

In the embodiments described herein where a swivel connector is attached to the fitness device and one or more rings are connected to the swivel connector, such as shown with respect to FIGS. 7A-7F, or in embodiments where the swivel connector is not required, such as shown with respect to FIGS. 12A and 12B, the end connectors of the wearable article may be various types of jewelry findings. For instance, as shown in FIGS. 14A and 14B, one or both of the end connectors may be a trigger clasp such as a lobster claw trigger clasp (FIG. 14A) or a caribiner trigger clasp (FIG. 14B). In further embodiments, the end connectors may be toggle clasps as shown in FIG. 14C, where the member slips through one of the rings connected to the swivel connector as is known in the jewelry art. In other embodiments, the end connectors may be spring biased ring clasps as shown in FIG. 14D. In other embodiments, the end connector may be a foldover clasp as shown in FIG. 14E.

Figure 14H:
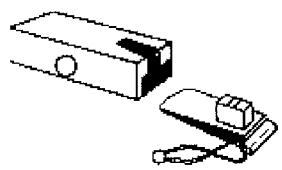
Figure 14G:
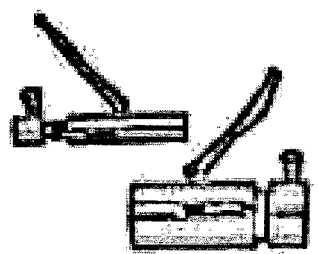
Figure 14I:
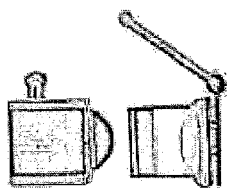
Figure 14J:

In additional embodiments, other types of jewelry findings may be used. For instance, FIG. 14F shows corresponding portions of a magnetic jewelry clasp. FIG. 14G shows corresponding portions of a barrel clasp. FIG. 14H shows portions of a box and tongue clasp. FIG. 14I shows corresponding portions of a solder-on box clasp. FIG. 14J shows portions of an easy snap clasp.

In the clasps shown in FIGS. 14F-14J, one portion is connected to the wearable article, and the corresponding portion is connected to the fitness device, either directly to the connector, of, for instance, to a ring attached to the connector of the fitness device. The portions may be connected by solder or by crimping. In further embodiments, the corresponding portion (not attached to the wearable article) is attached to a short chain, for instance, having one end being the suitable corresponding clasp portion and the other end being a connector such as shown with respect to FIGS. 14A-14E, that directly connects to the fitness device. In further alternative embodiments, the corresponding clasp portion of the embodiments of FIGS. 14F-14J (not attached to the wearable article) may be incorporated in a socket connector, for instance, in a manner similar to the sockets shown in FIGS. 13E and 13F.

Figure 15:
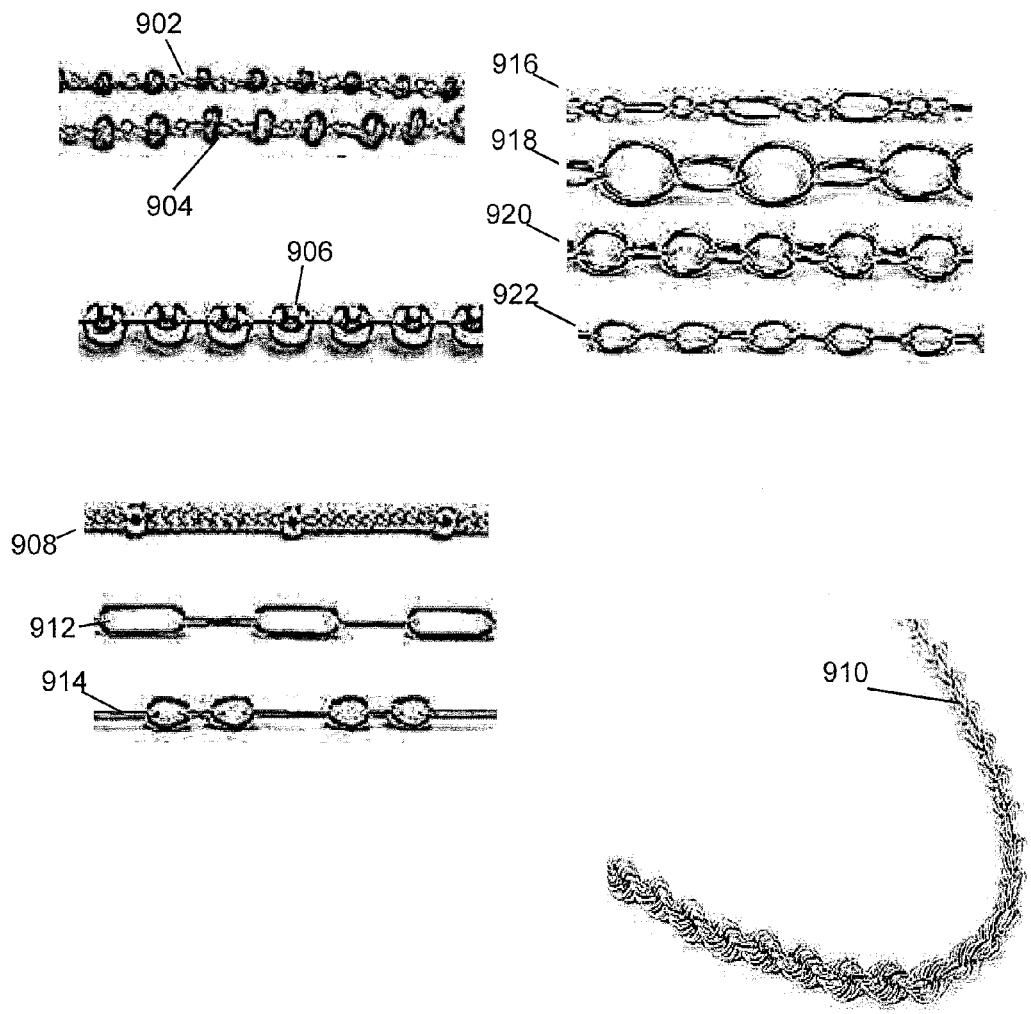
FIG. 15 shows various types of chains according to certain embodiments of the wearable fitness device.

Referring to FIG. 15, in embodiments where the wearable article includes an anklet and/or a bracelet, the wearable article may take the form of one or more various styles of links, chains, beads, or other decorative wearable articles. In certain embodiments described herein, a kit is provided allowing a wearer to easily change the style/shape/color of the wearable article using the same fitness device. For instance, the wearable article can take the form of various beads or other ornamental elements stringed on a suitable holding string or chain, such as beaded chains 902, 904 and 906. In other embodiments, various rope chains can be provided, such as chains 908, 910. In further embodiments, various shapes, sizes and styles of links can be provides, such as chains 912, 914, 916, 918, 920 and 922. A kit may comprise a combination of one or more of the above described chains, as well as one or more other style wearable articles as described further herein.

Described herein are various types of adjustability of the anklets. For instance, embodiments are shown with plural rings, where the wearable article connects to one of the rings and the others hand freely. In another embodiment, various length sockets are shown. In further embodiments, features used in existing adjustable chains, bracelets and anklets may be incorporated. For instance, such features are shown in U.S. Pat. Nos. 1,124,518, 1,459,670, 2,462,425, 4,321,804, 4,334,413, and 6,564,582, all of which are incorporated herein by reference.

Figure 16:
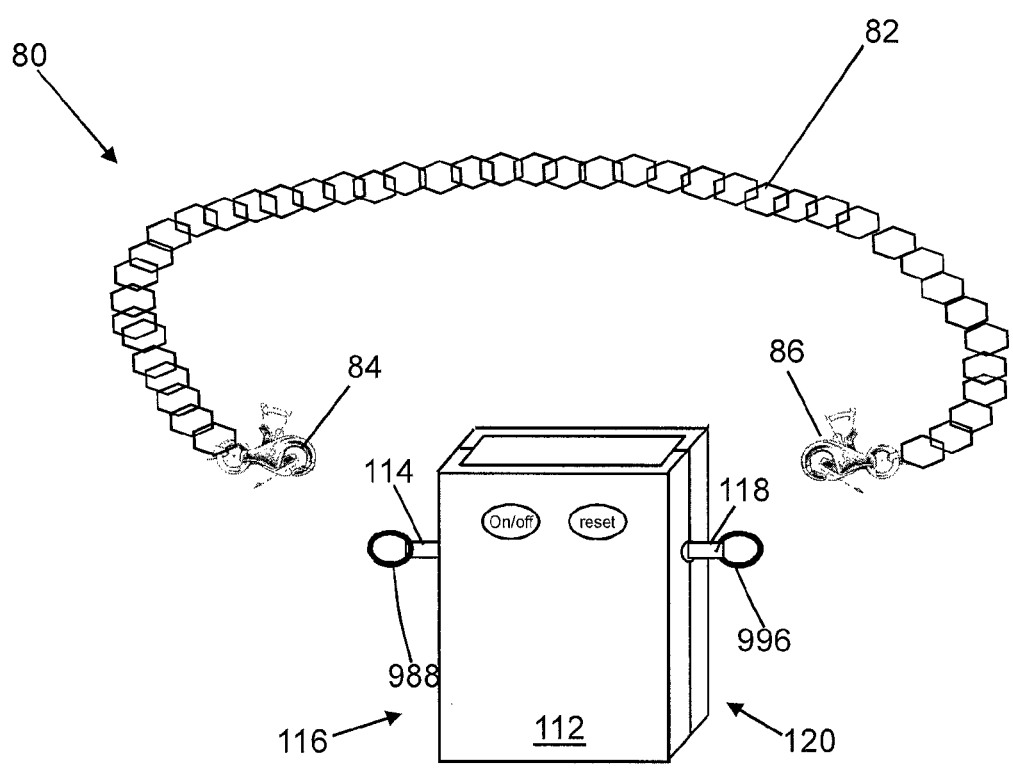
FIG. 16 shows an alternative embodiment of a fitness device having an adjustment structure.

FIG. 16 shows another embodiment of a wearable fitness device, similar to that shown with respect to FIGS. 7A-7F, with an additional feature for adjustability. Here, one ring is provided on each side (rings 988 and 996), which comprise elastic ring members. In this manner, adjustability may be provided without the need for excess rings. In certain embodiments, the elastic ring members may have conventional rings attached, e.g., metallic jewelry rings, opposite the side of the ring adjacent the fitness device 112, for instance, to facilitate connection to connectors 84, 86. Also, while swivel connectors 114, 118 are shown, the elastic ring members may be connected to fixed rings or other structures (such as the inset bars), since the elasticity will allow them to twist and maintain proper orientation as well as provide adjustable length.

As used herein, the term "fitness device" may refer to any suitable device for assisting in one's maintenance of personal fitness. The fitness device may include devices used to measure one's distance traversed, such as pedometers or accelerometers, heart rate monitors, blood pressure monitors, or any such device which measures or records static or active body parameters. In certain preferred embodiments herein, the fitness devices include those used to measure one's distance traversed is a pedometer such as a mechanical pedometer, an electro-mechanical pedometer, an electronic pedometer, or an accelerometer.

Although most known pedometers require proper orientation during use, it is to be understood that the present invention contemplates pedometers and/or accelerometers touted as functioning regardless of orientation, such as a vibration-detecting pedometer, such as the device disclosed in U.S. Pat. No. 6,836,524 to Lee issued on Dec. 28, 2004 entitled "Pedometer for detecting vibrations in the motion direction".

Further, accelerometers may be desired for incorporation into a wearable article due to their small size, and in certain embodiments, lack of requirement for orientation, to allow for a simpler and more aesthetically pleasing device. For example, one suitable accelerometer may include Mesmic, Inc. model MXC6202G/H/M/N (North Andover, Mass.) (e.g., as described in the specification sheet Rev.B dated Nov. 10, 2005). Further, a small compact accelerometer used to measure one's distance traversed can readily be attached and removed from one style or type of wearable article to another.

In particular, certain solid-state accelerometers are desirable, such as those that that senses acceleration along an acceleration sensing axis. Certain accelerometers employ a strain gauge for detecting the displacement of the weight supported by a spring. Alternatively, a piezoelectric element may be used in place of the spring, which piezoelectric element can measure the acceleration in terms of the electricity, which appears across the element in proportion to the displacement of the weight. In further alternatives, a suitable accelerometer uses a coil-and-weight in a magnetic field for inducing electromotive force in the coil moving in the magnetic field, thereby measuring acceleration in terms of the induced electromotive force.

Various types of displays are available on existing distance measuring devices such as pedometers or accelerometers, including mechanical or electronic displays. In certain preferred embodiments, for convenience of tabulation of distance traversed, a display may comprise a series of small lights (e.g., LED or LCD) that light up as desired intervals are achieved. For example, to correspond to the recommended 10,000 steps per day, five lights may be provided, whereby each indicated a 2000 step interval. This will enhance the aesthetic appeal of the device and minimize intrusion due to extended readouts and the like. Further, a device may also be programmed to read out a pattern of interim light sequences to indicate to the user their progressing within each 2000 step interval.

As described herein, in certain embodiments, a fitness device such as a pedometer may require accuracy of position within a zone of the body. As an example, if the device is a mechanical or electro-mechanical pedometer used as an anklet, the pedometer is preferably to be positioned and remain on the front side of the ankle so as to cause the mechanical device to record each leg movement. For example, accuracy is maintained in the system herein using the elastic or adjustable band to hold the wearable article incorporating the fitness device in place.

Further, as described herein, the fitness device, such as a pedometer, typically requires accuracy of orientation during wear. Orientation must be correct when the wearer puts the fashion device on. Various pockets, clip structures, securing structures, and the like are described herein. In certain preferred embodiments, these various pockets, clip structures, securing structures, and the like provide one-way connections between the fashion portion and fitness device. Further, alignment marks are also described above for ensuring proper orientation.

Additionally, various embodiments hereof enhance comfort. Comfort is desired to allow the wearer to use the fitness device more frequently, even during all waking hours of the day. As described above, the fitness device (e.g., pedometer, accelerometer) may be formed in a suitable housing curved appropriately to fit comfortably against the body. Further, the wearable article may include a suitable core that flexes to allow for comfortable movement of the wearer. Flexibility may be achieved by elastic, springs, or other such flexible materials or configurations.

Finally, a key feature of the present invention is its fashion flexibility. Certain embodiments describe systems that allow one fitness device to be interchangeable with plural wearable articles. This allows one to conveniently and fashionably use of the fitness device during different parts of the day. This is accomplished, e.g., with the interchangeable fitness device with multiple fashion portions, so that the fitness device can be changed between from one fashion type to another during the course of the wearer's day, allowing the wearer to measure a complete day of data on a single fitness device. This option would work well for wearers who switch outfits during the day. For example, business clothes during the day for work, casual clothes in the afternoon for home and dress clothes for evening. Additionally, the option of designs suitable for clubs, corporations, political activities, etc., such as used in marketing materials, are readily incorporated into this device.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A fitness accessory kit comprising:
   a first wearable article; and
   a fitness device for measuring cumulative distance traversed or number of steps by a person selected from the group consisting of mechanical pedometers, electro-mechanical pedometers, electronic pedometers, and accelerometers, the fitness device comprising a display having plurality of lights that are configured for illumination as fitness intervals are achieved by a user,
constructed and arranged to be removably attached to the first wearable article;
includes swivel connectors at two opposing lateral sides of the fitness device;
wherein each of the swivel connectors include a distal cross member having an internal stem extending therefrom with a shoulder, wherein a portion of a housing of the pedometer is rotatably seated on the internal stem, and an external stem extending from the shoulder with an aperture therethrough for receiving a ring, and wherein the wearable article includes end connectors that removably attach to the ring attached to each of the swivel connectors.

2. The fitness accessory kit as in claim 1, wherein the first wearable article is an anklet.

3. The fitness accessory kit as in claim 2, wherein the fitness device includes the display at a top portion thereof when the first wearable article is worn by a user.

4. The fitness accessory kit as in claim 1, wherein a plurality of rings are attached to each of the swivel connectors.

5. The fitness accessory kit as in claim 2, wherein the anklet is formed of chain links, beads, or rope chain.

6. The fitness accessory kit as in claim 2, wherein the anklet is formed of spandex fiber, knitted elastics, net elastics, rubber-based articles or stretchable cloth.

7. The fitness accessory kit as in claim 2, wherein the anklet includes an elastic or spring core.

8. The fitness accessory kit as in claim 1, comprising plural wearable articles including at least the first wearable article and a second wearable article, wherein the fitness device is constructed and arranged to be interchangeably connected between the first wearable article and the second wearable article.

9. The fitness accessory kit as in claim 8, wherein the plural wearable articles comprise plural types of wearable articles.

10. The fitness accessory kit as in claim 8, wherein the plural wearable articles comprise plural styles or colors of one type of wearable articles.

11. The fitness accessory kit as in claim 1, wherein the fitness device is a mechanical pedometer or an electro-mechanical pedometer.

12. The fitness accessory kit as in claim 1, wherein the fitness device is an electronic pedometer or an accelerometer.

13. The fitness accessory kit as in claim 1, comprising at least two connection structures on one or both sides of the fitness device, wherein the swivel connectors at the two opposing lateral sides of the fitness device form at least one of said connection structures the two opposing lateral sides of the fitness device, and the first wearable article comprises at least two end connectors on each end that removably attach to the at least two connection structures.

* * * * *